(12) United States Patent
Sanai et al.

(10) Patent No.: US 10,966,777 B2
(45) Date of Patent: Apr. 6, 2021

(54) TREATMENT DEVICE

(71) Applicant: OLYMPUS CORPORATION, Hachioji (JP)

(72) Inventors: Hideo Sanai, Hachioji (JP); Kenichi Kimura, Hachioji (JP); Masashi Yamada, Sagamihara (JP); Masami Oshida, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 372 days.

(21) Appl. No.: 16/002,759

(22) Filed: Jun. 7, 2018

(65) Prior Publication Data

US 2018/0280073 A1 Oct. 4, 2018

Related U.S. Application Data

(63) Continuation of application No. PCT/JP2016/086432, filed on Dec. 7, 2016.

(30) Foreign Application Priority Data

Dec. 7, 2015 (JP) .............................. JP2015-238791

(51) Int. Cl.
*A61B 17/32* (2006.01)
*A61B 18/14* (2006.01)
(Continued)

(52) U.S. Cl.
CPC .............. *A61B 18/14* (2013.01); *A61B 17/32* (2013.01); *A61B 17/320068* (2013.01);
(Continued)

(58) Field of Classification Search
CPC . A61B 17/32; A61B 17/320068; A61B 18/14; A61B 2017/00039;
(Continued)

(56) References Cited

U.S. PATENT DOCUMENTS

2008/0294051 A1 11/2008 Koshigoe et al.
2009/0216257 A1 8/2009 Sanai et al.
2014/0324084 A1* 10/2014 Sanai ................. A61B 18/1482
606/169

FOREIGN PATENT DOCUMENTS

CN 101518463 A 9/2009
EP 2 100 563 A1 9/2009
(Continued)

OTHER PUBLICATIONS

Jun. 12, 2018 International Preliminary Report on Patentability issued in International Patent Application PCT/JP2016/086432.
Dec. 12, 2017 Office Action issued in Japanese Patent Application No. 2017-547027.
Apr. 26, 2020 Office Action issued in Chinese Patent Application No. 201680071637.7.
(Continued)

*Primary Examiner* — Michael F Peffley
*Assistant Examiner* — Amanda L Zink
(74) *Attorney, Agent, or Firm* — Oliff PLC

(57) ABSTRACT

A treatment device includes a vibrator capable of ultrasonically vibrating, a front mass portion having a first resonance frequency and connected to the vibrator in a manner capable of transmitting ultrasonic vibration, a treatment probe configured to treat a subject and having a second resonance frequency that is higher than the first resonance frequency of the front mass portion, and a connection portion connecting a distal end surface of the front mass portion and a proximal end surface of the treatment probe by a pressing force, and serving as an antinode position when vibrating at the first resonance frequency.

7 Claims, 13 Drawing Sheets

(51) Int. Cl.
    *A61N 7/02* (2006.01)
    *A61B 17/00* (2006.01)
    *A61B 18/00* (2006.01)

(52) U.S. Cl.
    CPC ...... *A61N 7/02* (2013.01); *A61B 2017/00039* (2013.01); *A61B 2017/0042* (2013.01); *A61B 2017/00473* (2013.01); *A61B 2017/00477* (2013.01); *A61B 2017/00845* (2013.01); *A61B 2018/00607* (2013.01); *A61B 2018/00791* (2013.01); *A61B 2018/00994* (2013.01)

(58) Field of Classification Search
    CPC .. A61B 2017/0042; A61B 2017/00473; A61B 2017/00477; A61B 2017/00845; A61B 2018/00607; A61B 2018/00791; A61B 2018/00994; A61N 7/02
    See application file for complete search history.

(56) References Cited

FOREIGN PATENT DOCUMENTS

| JP | H02-203972 A | 8/1990 |
| JP | H02-123216 U | 10/1990 |
| JP | H05-49649 A | 3/1993 |
| JP | 2009-201984 A | 9/2009 |
| WO | 2015/072326 A1 | 5/2015 |
| WO | 2015/122307 A1 | 8/2015 |

OTHER PUBLICATIONS

May 27, 2019 Search Report issued in European Patent Application No. 16873035.6.

Mar. 7, 2017 International Search Report issued in International Patent Application PCT/JP2016/086432.

* cited by examiner

|  | Frequency difference[kHz] (Probe −F mass) | Abnormal noise (magnitude) | | |
|---|---|---|---|---|
|  |  | First measurement | Second measurement | Third measurement |
| Sample1 | 0.06 | 0 | 0 | 0 |
| Sample2 | 0.01 | 0 | 0 | 0 |
| Sample3 | 0.06 | 0 | 0 | 0 |
| Sample4 | −1.83 | 0 | 3 | 0 |
| Sample5 | −1.87 | 0 | 0 | 2 |
| Sample6 | −1.83 | 0 | 0 | 0 |
| Sample7 | −1.51 | 0 | 0 | 0 |
| Sample8 | −1.50 | 0 | 0 | 0 |
| Sample9 | −1.52 | 0 | 0 | 0 |
| Sample10 | −1.21 | 0 | 0 | 0 |
| Sample11 | −1.21 | 0 | 0 | 0 |
| Sample12 | −1.23 | 0 | 0 | 0 |
| Sample13 | −0.94 | 0 | 0 | 0 |
| Sample14 | −0.98 | 0 | 0 | 0 |
| Sample15 | −0.97 | 0 | 0 | 0 |
| Sample16 | 0.82 | 0 | 0 | 0 |
| Sample17 | 0.78 | 0 | 0 | 0 |
| Sample18 | 0.78 | 0 | 0 | 0 |
| Sample19 | 1.09 | 0 | 0 | 0 |
| Sample20 | 1.07 | 0 | 0 | 0 |
| Sample21 | 1.07 | 0 | 0 | 0 |
| Sample22 | 1.41 | 0 | 1 | 0 |
| Sample23 | 1.31 | 0 | 0 | 0 |
| Sample24 | 1.36 | 0 | 0 | 0 |
| Sample25 | 1.63 | 0 | 0 | 0 |
| Sample26 | 1.58 | 0 | 0 | 0 |
| Sample27 | 1.58 | 0 | 0 | 0 |

0 ··· No abnormal noise
1 ··· Abnormal noise present − small
2 ··· Abnormal noise present − medium
3 ··· Abnormal noise present − large

F I G. 7

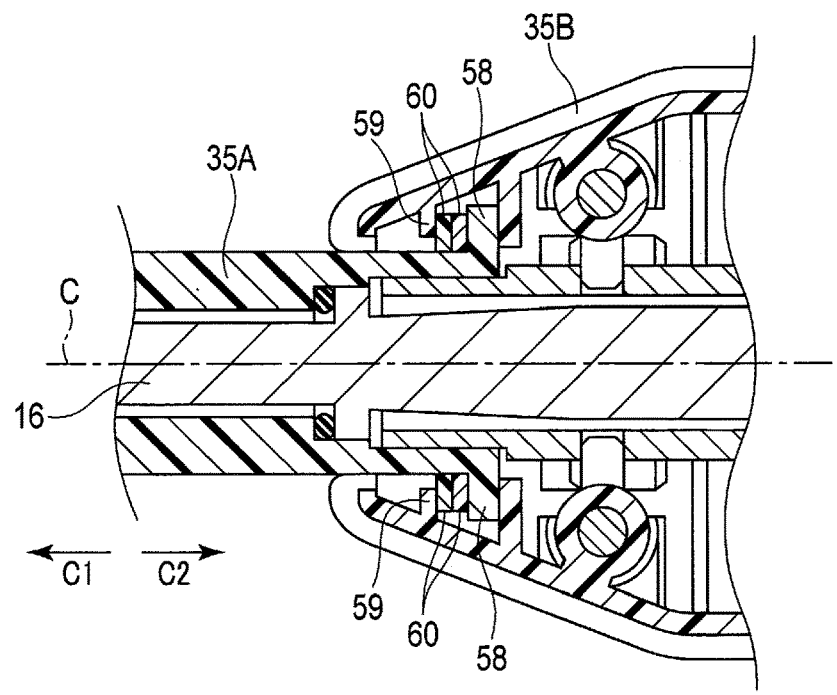
F I G. 12
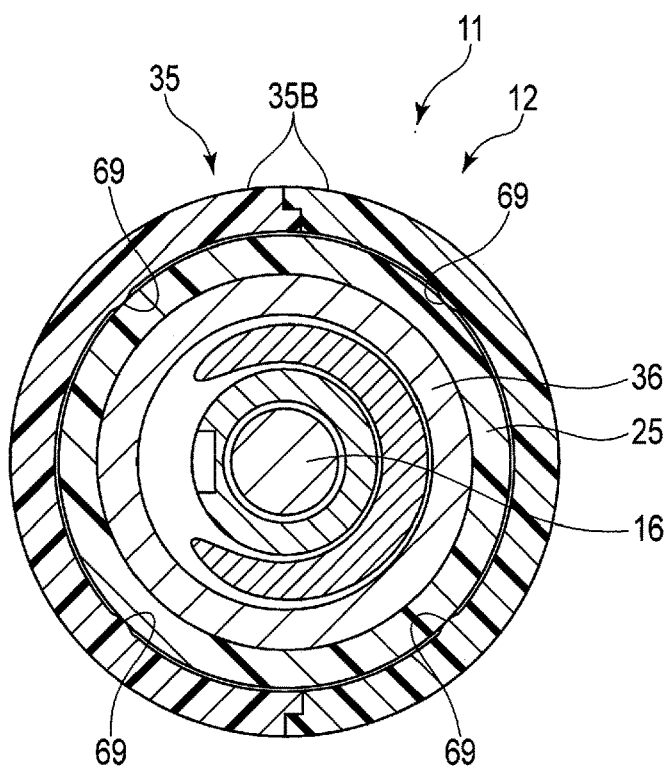
F I G. 13

TREATMENT DEVICE

CROSS-REFERENCE TO RELATED APPLICATIONS

This application is a Continuation Application of PCT Application No. PCT/JP2016/086432, filed Dec. 7, 2016 and based upon and claiming the benefit of priority from prior Japanese Patent Application No. 2015-238791, filed Dec. 7, 2015, the entire contents of all of which are incorporated herein by reference.

BACKGROUND OF THE INVENTION

1. Field of the Invention

The present invention relates generally to a treatment device for treating a living tissue with energy such as ultrasonic vibration.

2. Description of the Related Art

A general ultrasonic therapeutic device is disclosed in Japanese Patent Appln. KOKAI Publication No. H5-49649 (Patent Document 1). In this ultrasonic therapeutic device, ultrasonic vibration is used to cut or emulsify a living tissue.

BRIEF SUMMARY OF THE INVENTION

A treatment device according to one embodiment of the present invention includes a vibrator capable of ultrasonically vibrating, a front mass portion having a first resonance frequency and connected to the vibrator in a manner capable of transmitting ultrasonic vibration, a treatment probe configured to treat a subject and having a second resonance frequency that is higher than the first resonance frequency of the front mass portion, and a connection portion connecting a distal end surface of the front mass portion and a proximal end surface of the treatment probe by a pressing force, and serving as an antinode position when vibrated at the first resonance frequency.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 7 is a table showing the presence or absence of abnormal noise and the magnitude of abnormal noise in a case where the frequency difference between the first resonance frequency (front mass portion) and the second resonance frequency (probe) is changed.

FIG. 12 is an enlarged cross-sectional view around a low friction member of the treatment device shown in FIG. 11.

FIG. 13 is a cross-sectional view taken along a line F13-F13 shown in FIG. 11.

DETAILED DESCRIPTION

First Embodiment

A first embodiment of the present invention will be explained with reference to FIGS. 1 to 7.

Figure 1:
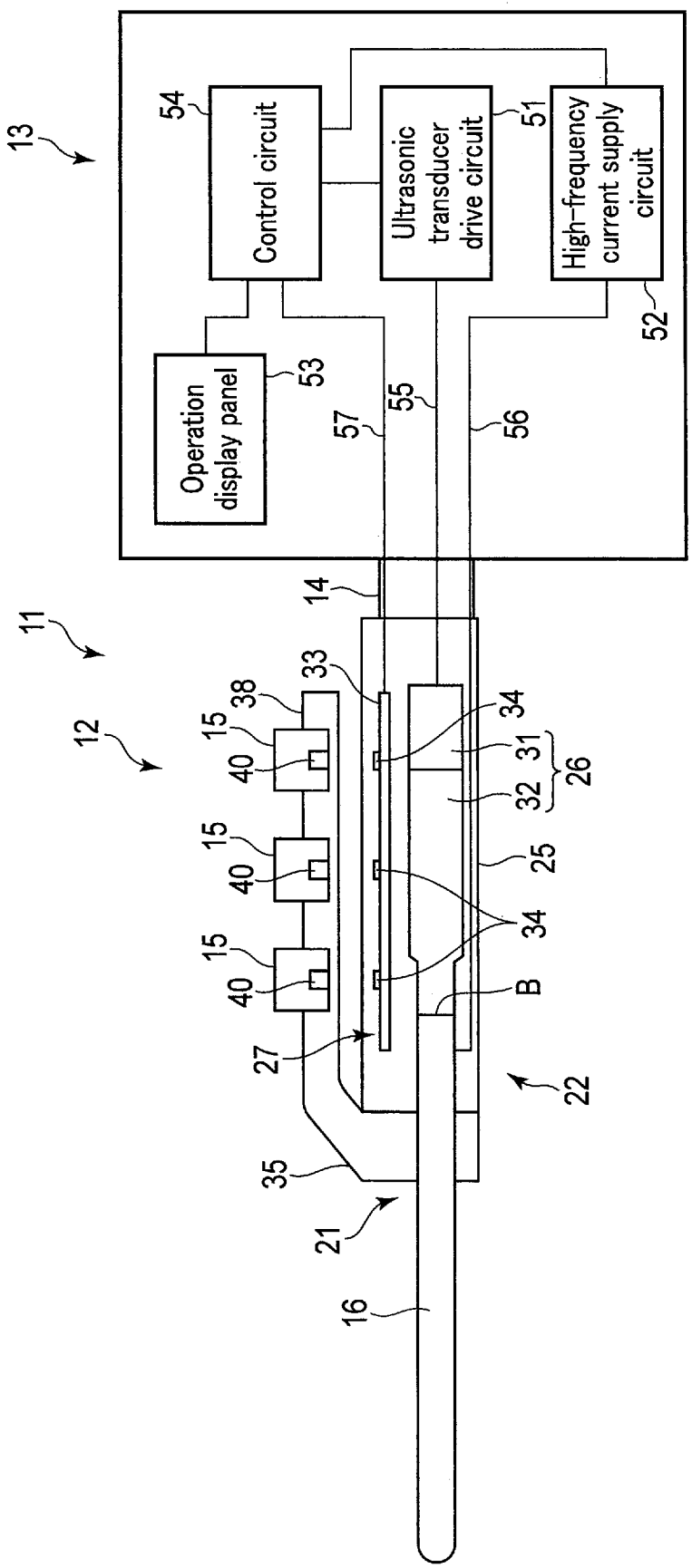
FIG. 1 is a schematic diagram showing the entire configuration of a treatment device of a first embodiment.

As shown in FIG. 1, a treatment device 11 includes a handpiece 12, a power supply device 13, and a cable 14 that connects the handpiece 12 and the power supply device 13. The power supply device 13 is capable of supplying energy to the handpiece 12 in accordance with the operation of an operation button 15 (operation portion) of the handpiece 12. In the present embodiment, one of two directions parallel to a longitudinal direction C of a probe 16 provided in the handpiece 12 is referred to as a distal end direction C1, and the direction opposite to the distal end direction C1 is referred to as a proximal end direction C2.

As shown in FIGS. 1 to 4, the handpiece 12 includes a probe unit 21 (disposable portion) including the probe 16 (treatment probe) for performing treatment on a living body tissue of a patient, and a grip unit 22 (reuse portion) that is detachable to the probe unit 21. As will be described in detail later, the probe unit 21 and the grip unit 22 are fixed by a so-called non-threaded connection by a cam structure via a pin 23 and a receiving portion 24.

As shown in FIG. 1, the grip unit 22 includes a substantially cylindrical housing 25 configuring an outer shell, a vibration generation unit 26 accommodated in the housing 25, the receiving portion 24 provided inside the housing 25 on which the pin 23 on the probe unit 21 side is hooked, and a detection unit 27 capable of detecting the operation of the operation button 15 of the probe unit 21. The grip unit 22 can be reused by sterilizing it with an autoclave or the like after being cleaned. On the other hand, the probe unit 21 is used only once.

The vibration generation unit 26 includes an ultrasonic transducer 31 (vibrator) accommodated in the housing 25 and a front mass portion 32 including a horn member connected to the ultrasonic transducer 31. The ultrasonic transducer 31 includes a plurality of (eight in this embodiment) piezoelectric elements 31A, and is capable of generating ultrasonic vibration by the piezoelectric elements 31A that have received power supply from an ultrasonic transducer drive circuit 51. The resonance frequency (a first resonance frequency) of the vibration generation unit 26 (ultrasonic vibration generated by the ultrasonic transducer 31) is, for example, 47 kHz. The front mass portion 32 is formed of a titanium-based alloy, but may be formed of other metal materials such as duralumin, stainless steel or the like, other than the titanium-based alloy. The front mass portion 32 is provided with a substantially conical cross-section changing part whose cross-sectional area decreases toward the distal end direction C1 of the probe 16. The ultrasonic vibration generated by the ultrasonic transducer 31 is transmitted to the front mass portion 32. At the cross-section changing part, the amplitude of the ultrasonic vibration is expanded.

Figure 2:
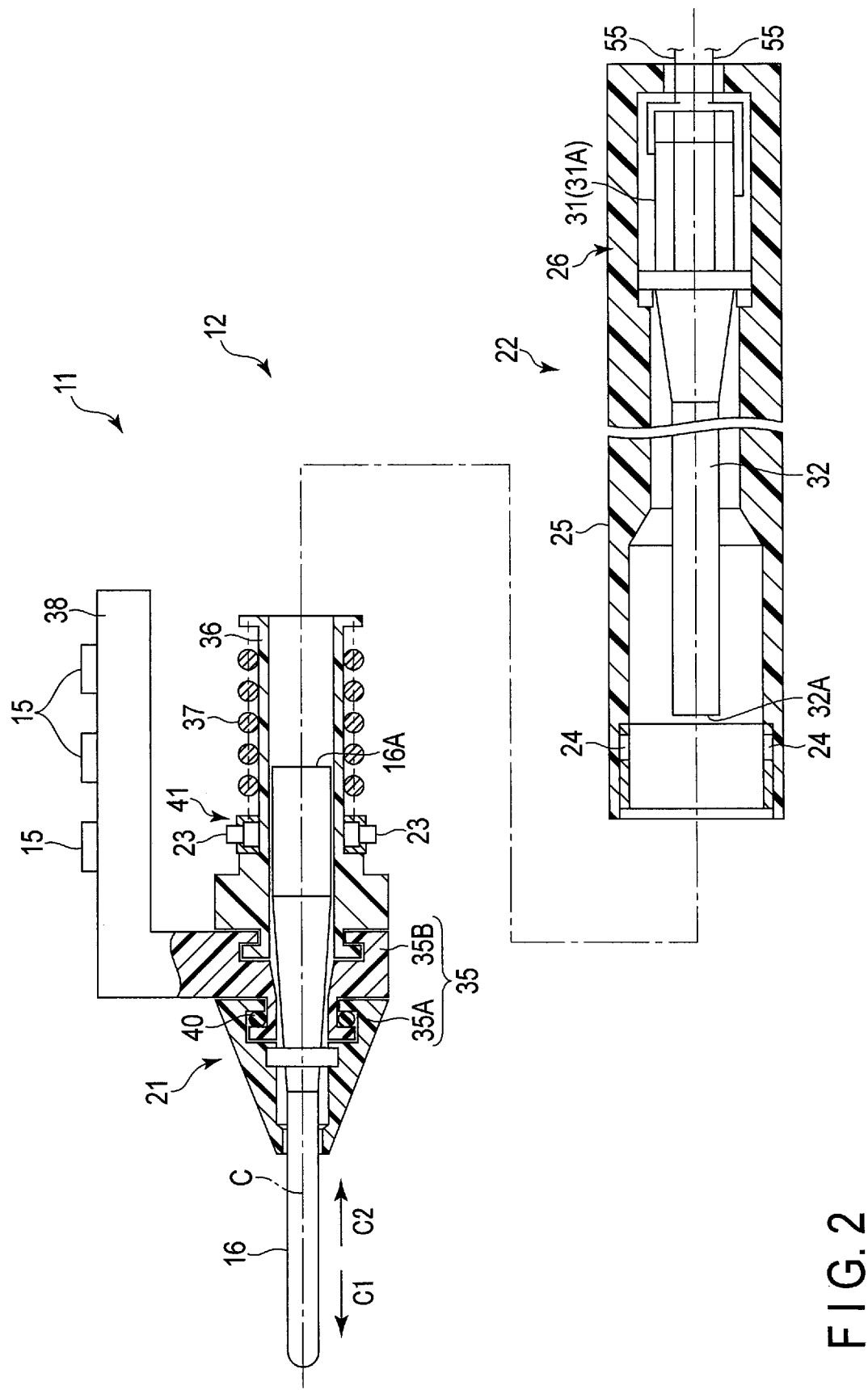
FIG. 2 is a schematic diagram showing a state in which a probe unit and a grip unit of a handpiece shown in FIG. 1 are separated.
Figure 3:
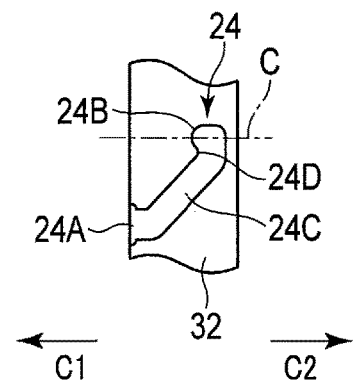
FIG. 3 is a schematic diagram showing a part of a receiving portion of the grip unit of the treatment device shown in FIG. 1.

As shown in FIGS. 2 and 3, three pieces of receiving portion 24 are provided so as to correspond respectively to a total of three pins 23 provided on the probe unit 21 side and extending in a radial direction of the probe 16. The receiving portions 24 have the same shape. The receiving portion 24 is formed in a groove shape onto which the pin 23 may be hooked. The receiving portion 24 includes an introduction portion 24A into which the pin 23 is first inserted, a holding portion 24B provided at the back of the groove configuring the receiving portion 24, a guide portion 24C connecting the introduction portion 24A and the holding portion 24B, and a protruded portion 24D provided at a boundary between the holding portion 24B and the guide portion 24C.

As shown in FIG. 1, the detection unit 27 includes a printed board 33 accommodated in the housing 25 and a plurality (three) of detection portions 34 mounted on the printed board 33. The detection portion 34 is a non-contact type sensor (magnetic sensor) that is provided separately from the operation button 15 on the probe unit 21 side, and is capable of detecting an operation of the operation button 15 based on the position of a detection target portion 40 (magnet) of the operation button 15. In the present embodiment, the detection portion 34 is formed of an integrated circuit on which a magnetic detection element, such as a Hall element, is mounted. If the strength of the magnetic field detected by the Hall element exceeds a prescribed threshold value, the integrated circuit outputs a prescribed voltage corresponding to an energy supply start signal. On the other hand, if the strength of the magnetic field detected by the Hall element falls below the prescribed threshold value, the integrated circuit outputs a prescribed voltage corresponding to an energy supply stop signal.

Figure 10:
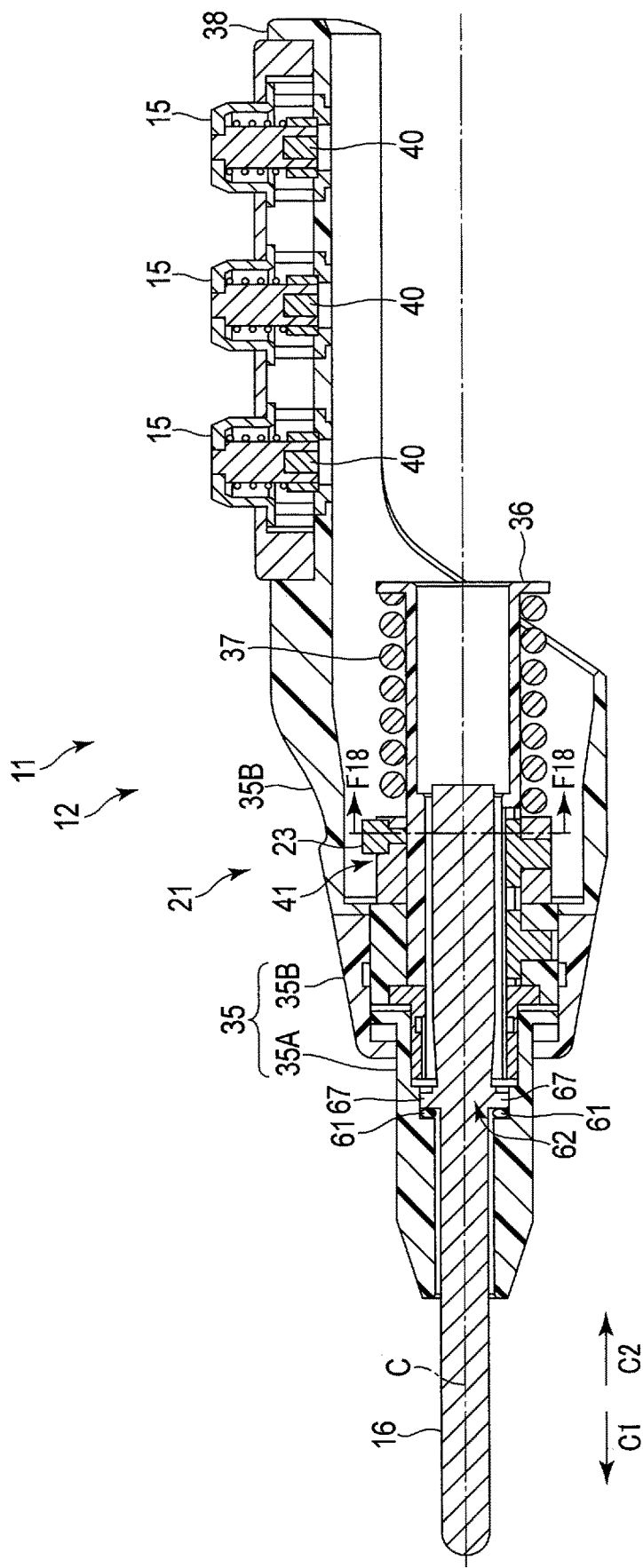
FIG. 10 is a cross-sectional view of a treatment device of a first modified example and a second modified example taken along a plane along a central axis.

As shown in FIGS. 1 and 2, the probe unit 21 includes the probe 16, a case 35 that covers the periphery of the probe 16, a cylindrical member 36 that is integrally formed with the probe 16 and the case 35, a spring member 37 that is provided on the periphery of the cylindrical member 36, a pin unit 41 that is slidably movable with respect to the cylindrical member 36 and is pressed toward the distal end direction C1 by the spring member 37, a plate-like button support portion 38 that is provided so as to protrude from an end part of the case 35, a plurality of (for example, three) operation buttons 15 (operation portion) provided on the button support portion 38, and a second spring member that applies repulsive force to the operation buttons 15 (see FIG. 10). The spring member 37 is formed of a compression coil spring. The pin unit 41 includes a plurality of (for example, three) pins 23 protruding in the radial direction of the probe 16.

Figure 4:
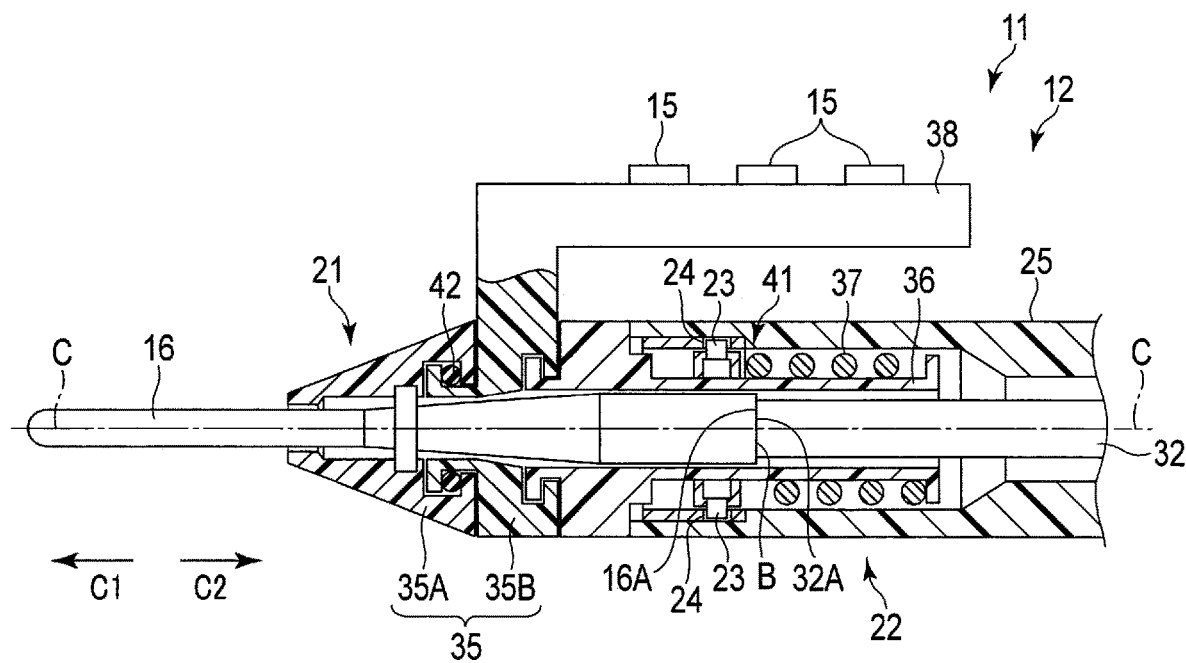
FIG. 4 is a schematic diagram showing a state in which the probe unit and the grip unit of the handpiece shown in FIG. 2 are fixed.

As shown in FIGS. 2 and 4, the probe 16 (treatment portion) is formed rod-like by a metallic material having, for example, biocompatibility (for example, titanium, a titanium alloy, duralumin, and stainless steel). The probe 16 is capable of treating a subject by the transmitted ultrasonic vibration. For example, the resonance frequency (second resonance frequency) of the probe 16 is set to become 47.5 kHz, which is higher than the first resonance frequency of the vibration generation unit 26, in the initial state (the state before the surgeon uses the treatment device 11). A proximal end surface 16A of the probe 16 abuts against a distal end surface 32A of the front mass portion 32 and is joined. The force with which the proximal end surface 16A of the probe 16 is pressed against the distal end surface 32A of the front mass portion 32 is 100 to 200 N. Ultrasonic vibration is transmitted from the ultrasonic transducer 31 to the probe 16 and a high-frequency current is supplied from a high-frequency current supply circuit 52 via a second conducting wire 56 to the probe 16. Therefore, the probe 16 not only can apply ultrasonic vibration to a living tissue but also can function as an active electrode for monopolar treatment. The treatment device 11 further includes a return electrode plate that is placed outside the body of a patient, and functions as the other electrode of the monopolar treatment.

The case 35 is made of, for example, a synthetic resin material. The case 35 includes a first portion 35A that configures a rotation knob for rotating the probe 16 around the central axis C, a second portion 35B, and a plurality of balls 42 that are interposed in a connecting portion between the first portion 35A and the second portion 35B. The first portion 35A is fixed to the probe 16 so as to be integrated with the probe 16, and configures a rotation knob for rotating the probe 16 around the central axis C. The plurality of balls 42 are provided around the central axis C at appropriate intervals, in order to reduce friction between the first portion 35A and the second portion 35B.

As shown in FIG. 2, the button support portion 38 is provided integrally with the second portion 35B. The button support portion 38 includes a base portion molded integrally with the case 35 and a cover covering the upper side of the base portion. The three operation buttons 15 and the three second spring members are held between the base portion and the cover (see FIG. 10). On the bottom portion of the operation button 15, the detection target portion 40 that is detected by the detection unit 27 on the grip unit 22 side is provided.

In the present embodiment, the operation button 15 located closest to the distal end direction C1 corresponds to, for example, a cut mode for cutting and cutting off a living tissue using high-frequency energy and ultrasonic energy. The operation button 15 at the center corresponds to, for example, a first coagulation mode in which coagulation of a living tissue is performed using two types of energy of the high-frequency energy and the ultrasonic energy. The operation button 15 closest to the proximal end direction C2 corresponds to a second coagulation mode in which coagulation of a living tissue is performed using, for example, high-frequency energy. The function corresponding to the above-described operation button 15 is an example. The function corresponding to each operation button 15 can be set/changed appropriately by using an operation display panel 53 of the power supply device 13.

A procedure for attaching the probe unit 21 to the grip unit 22 will be explained. As shown in FIG. 2, the cylindrical member 36 is inserted into the housing 25, and the pin 23 is further aligned with and inserted into the introduction portion 24A of the receiving portion 24. Then, while pushing the grip unit 22 into the probe unit 21, the grip unit 22 is rotated with respect to the probe unit 21. When the grip unit 22 continues to rotate, the pin 23 passes through the guide portion 24C and reaches the holding portion 24B beyond the protruded portion 24D.

At this time, the tension generated by using the cam mechanism configured by the pin 23 and the receiving portion 24 is transmitted to the probe 16 via the spring member 37, which causes the probe 16 to be pressed against the front mass portion 32 and compresses the spring member 37.

As shown in FIG. 4, in a state where the proximal end surface 16A of the probe 16 abuts against the distal end surface 32A of the front mass portion 32 with a predetermined force (100 to 200 N), the ultrasonic vibration transmission from the front mass portion 32 to the probe 16 becomes possible. At this time, in a state where the front mass portion 32 and the probe 16 are joined (butted), the entire resonance frequency (third resonance frequency) obtained by combining the front mass portion 32 and the probe 16 is, for example, 47.2 kHz. The third resonance frequency satisfies the relationship of:

First resonance frequency≤Third resonance frequency≤Second resonance frequency    Formula (1).

Each of the above-mentioned numerical values of the first resonance frequency of the front mass portion 32, the second resonance frequency of the probe 16, and the entire combined third resonance frequency is merely an example, which can be set as appropriate to satisfy the relationship of Formula (1).

Figure 5:
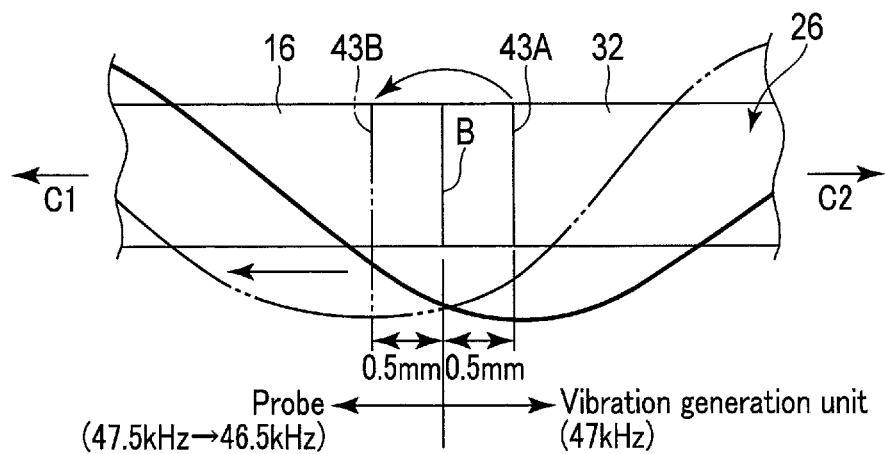
FIG. 5 is a schematic diagram showing an ultrasonic vibration wave (a waveform at the moment of a maximum amplitude) transmitted through a probe and a sheath member of the handpiece shown in FIG. 1.

A boundary surface B (connection portion) between the probe 16 and the front mass portion 32 configures a portion that presses and connects the distal end surface 32A of the front mass portion 32 and the proximal end surface 16A of the probe 16 (treatment probe), and becomes an antinode position when vibrating at the first resonance frequency described later on. In addition, the vicinity of an antinode position 43A of the ultrasonic vibration transmitted therethrough is designed to be positioned at the boundary surface B (connection portion). More specifically, as shown in FIG. 5, the antinode position 43A of the ultrasonic vibration in an initial state (a state before the temperature rises in the probe 16) is designed to be set at a position shifted 0.5 mm from the boundary surface B to the proximal end direction C2 side (to the vibration generation unit 26 side).

On the other hand, when detaching the probe unit 21 from the grip unit 22, the probe unit 21 can be easily detached from the grip unit 22 by rotating the probe unit 21 with respect to the grip unit 22 and causing the pin 23 to move against the pressing force of the spring member 37 in a manner to be removed from the receiving portion 24.

As shown in FIG. 1, the power supply device 13 includes an ultrasonic transducer drive circuit 51 (ultrasonic energy supply unit) for driving the ultrasonic transducer 31 of the handpiece 12, a high-frequency current supply circuit 52 (high-frequency energy supply unit) for supplying a high-frequency current (high-frequency energy) to the probe 16 of the handpiece 12, an operation display panel 53 for setting and displaying output levels of ultrasonic output and high-frequency output corresponding to each operation button 15 of the handpiece 12, and a control circuit 54 (controller) connected to them. The ultrasonic transducer drive circuit 51 is connected to the piezoelectric element 31A of the ultrasonic transducer 31 of the probe unit 21 by two first conducting wires 55 passing through the cable 14. The high-frequency current supply circuit 52 has one output terminal connected to the probe 16 of the probe unit 21 by a second conducting wire 56 passing through the cable 14, and the other output terminal connected to the counter electrode plate via a third conducting wire passing through a second cable. The control circuit 54 is connected to the detection unit 27 of the grip unit 22 by a plurality of fourth conducting wires 57 passing through the cable 14.

The control circuit 54 is connected to the ultrasonic transducer drive circuit 51 and the high-frequency current supply circuit 52. When the operation button 15 is operated by the doctor, an electric signal is transmitted to the control circuit 54, and the operation of the operation button 15 is detected. As a result, the control circuit 54 controls the ultrasonic transducer drive circuit 51 to supply the ultrasonic wave generation current to the piezoelectric element 31A, or controls the high-frequency current supply circuit 52 to supply the high-frequency current to the probe 16. As a result, the ultrasonic vibration or the high-frequency current is transmitted to the probe 16. Alternatively, the control circuit 54 simultaneously controls both the ultrasonic transducer drive circuit 51 and the high-frequency current supply circuit 52 to simultaneously supply both the ultrasonic vibration and the high-frequency current to the probe 16.

The operation display panel 53 is a touch panel that can make various settings, such as a setting of the output level of the ultrasonic wave output, a setting of the output intensity of the high-frequency current, and a setting of functions of the three operation buttons 15.

Next, with reference to FIG. 5, an operation of the treatment device 11 of the present embodiment will be explained. In the present embodiment, the resonance frequency of the probe 16 is designed to be higher than the resonance frequency of the vibration generation unit 26, to enable efficient transmission of the ultrasonic vibration after the change of the resonance frequency on the probe 16 side. In order to efficiently transmit the ultrasonic vibration from one side to the other side of the two members, it is effective to position the antinode position of the ultrasonic vibration in the vicinity of the boundary surface (bonding surface) of both members. On the other hand, if the node position of the ultrasonic vibration at which the stress becomes large is located near the boundary surface between the two members, the transmission loss of the ultrasonic vibration increases.

In the present embodiment, the resonance frequency of the vibration generation unit 26 (front mass portion 32) is 47 kHz (first resonance frequency). Furthermore, the resonance frequency of the probe 16 is 47.5 kHz (second resonance frequency) in the initial state (a state before a surgeon uses the treatment device 11). In the initial state, the ultrasonic vibration transmitted through the vibration generation unit 26 and the probe 16 has a waveform as indicated by a solid line at the moment of the maximum amplitude. The ultrasonic vibration antinode position 43A is located at a position deviated 0.5 mm from the boundary surface B of the vibration generation portion 26 and the probe toward the vibration generation unit 26 side. Although the ultrasonic vibration antinode position 43A is deviated from the boundary surface B in the initial state, the transmission loss of the vibration at the boundary surface B is minor because the displacement amount is minute.

When the surgeon starts treatment and the treatment device 11 is continuously used, the temperature of the probe 16 rises up to, for example, 200 to 400° C. from room temperature (initial state). In the case where the temperature of the probe 16 becomes high in this manner, the Young's modulus of the probe 16 changes, and the resonance frequency of the probe 16 decreases from 47.5 kHz (second resonance frequency) to, for example, a minimum value of 46.5 kHz. At this time, the decrease amount of the resonance frequency varies depending on the amount of rise in temperature of the probe 16. As the second resonance frequency decreases, the entire third resonance frequency of the combination of the front mass portion 32 and the probe 16 also decreases.

When the first resonance frequency of the probe 16 decreases to, for example, 46.5 kHz, the entire third resonance frequency also decreases, and the wave of the ultrasonic vibration transmitted through the vibration generation unit 26 and the probe 16 shifts as shown by a two-dot chain line to the probe 16 side. Therefore, the antinode position 43B of the ultrasonic vibration also moves to a position deviated 0.5 mm from the boundary surface B (joint surface) of the probe 16 and the vibration generation portion toward the probe 16 side. Also in this use state, although the antinode position 43B of the ultrasonic vibration is deviated from the boundary surface B, the transmission loss of the vibration at the boundary surface B is minor because the displacement amount is minute. Therefore, in the present embodiment, the antinode positions 43A and 43B of the ultrasonic vibration can be arranged near the boundary surface B before and after the change in the resonance frequency on the probe 16 side, which reduces the vibration transmission loss at the boundary surface B.

The extent of temperature rise of the probe 16 varies depending on the frequency of use. That is, in the case of a treatment in which the frequency of use per hour is high, the temperature rise of the probe 16 is large; however, in the case of a treatment in which the frequency of use per hour is low, the temperature rise of the probe 16 is small. In addition, in the present embodiment, the probe 16 and the vibration generation unit 26 are designed so as to satisfy the relationship of the first resonance frequency<the second resonance frequency<the first resonance frequency+1.5 kHz.

Figure 6:
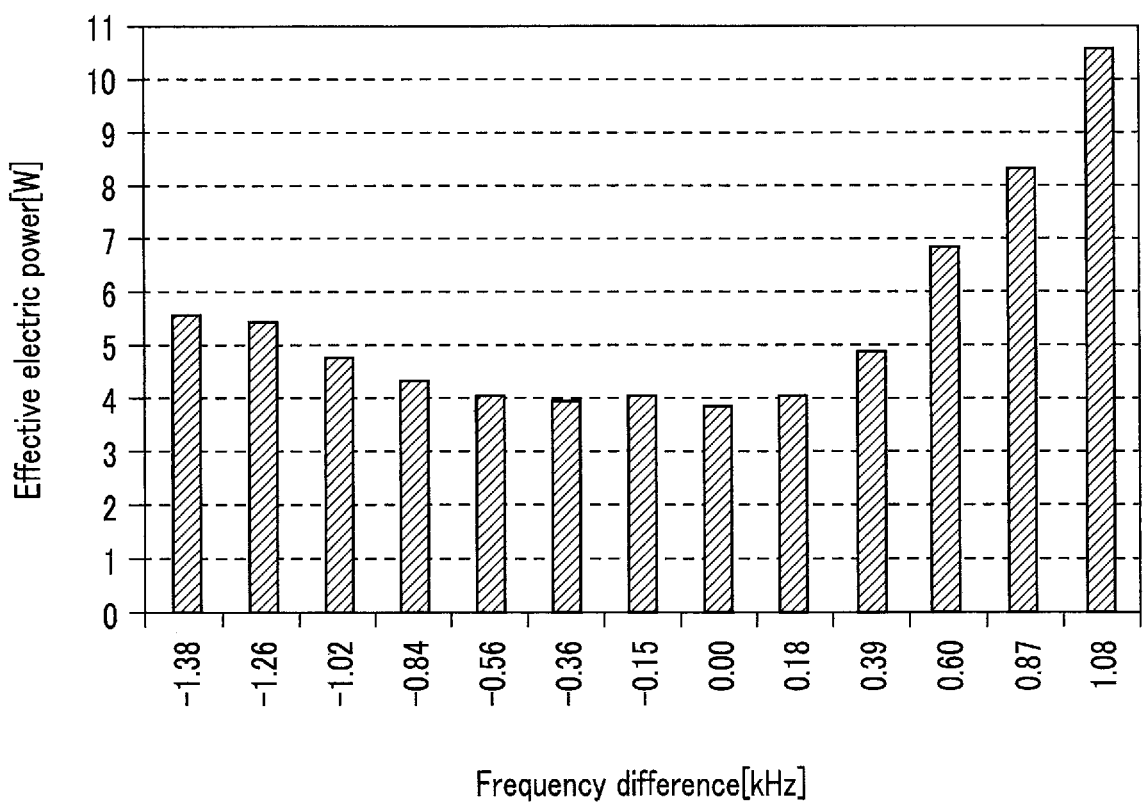
FIG. 6 is a graph showing changes in effective electric power in a case where a frequency difference between a first resonance frequency and a second resonance frequency in the treatment device of the first embodiment is changed from −1.38 to +1.08 kHz.

Prior to designing the probe 16, the front mass portion 32, and the vibration generation unit 26, the inventors conducted an experiment of measuring the power (effective electric power) consumed by the ultrasonic transducer 31 in the case where the frequency difference (a value obtained by subtracting the first resonance frequency from the second resonance frequency) is changed between the first resonance frequency of the front mass portion 32 and the second resonance frequency of the probe 16. As a result, as shown in FIG. 6, in the case where the frequency difference is 0 kHz, the effective electric power is slightly less than 4 W. In the case where the second resonance frequency is gradually reduced, the effective electric power gradually increases from around where the frequency difference falls below −0.84 kHz, and when the frequency difference becomes −1.38 kHz, the effective electric power becomes approximately 5.5 W. Instead, in the case where the second resonance frequency is gradually increased, the effective electric power increases quadratically, and when the frequency difference reaches +1.08 kHz, the effective electric power becomes approximately 10.5 W. Thus, it has been discovered that as the frequency difference deviates from 0, the value of the effective electric power increases, and the transmission loss at the connection portion occurs when the probe 16 is ultrasonically vibrated.

Similarly, the inventors conducted an experiment to evaluate the presence or absence of abnormal noise generated from the boundary surface B (connection portion) and the magnitude of the abnormal noise in the case where the frequency difference is changed. The results are shown in FIG. 7. Here, the frequency difference can be calculated by a formula such as, frequency difference=(second resonance frequency)−(first resonance frequency). The amplitude of the ultrasonic vibration at the boundary portion B (connection portion) was set to 15 μm. The evaluation of the presence or absence of the abnormal noise and the magnitude of the abnormal noise was made based on whether the noise felt small or large when listening with the human ear. When there was no abnormal noise, the noise was evaluated as 0 (no abnormal noise), and when there was an abnormal noise that can be heard by bringing the ear close to the boundary portion B (connection portion), however, cannot be heard upon actual use, the noise was evaluated as 1 (abnormal noise present—small). When an abnormal noise was clearly heard even if the current waveform of the ultrasonic vibration was not distorted, and was determined as being heard upon actual use (disturbing), the noise was evaluated as 2 (abnormal noise present—medium). When the current waveform of the ultrasonic vibration was distorted, and an abnormal noise was clearly heard as a large sound (a roaring noise was heard at the boundary portion B (connection portion)), the noise was evaluated as 3 (abnormal noise present—large). In the range of the frequency difference from −1.51 to +1.63 kHz (samples 1 to 3, 7 to 27), the evaluation result was that there was no abnormal noise. In sample 22 (frequency difference=1.41 kHz), the evaluation result of 1 (abnormal noise present—small) was obtained in the second measurement; however, since the abnormal noise was small, and the noise was evaluated as 0 in the first and third measurements (no abnormal noise), the evaluation result of 1 can be mostly ignored. In sample 4 (frequency difference=−1.83 kHz), the evaluation result of 3 (abnormal noise present—large) was obtained in the second measurement, and in sample 5 (frequency difference=−1.87 kHz), the evaluation result of 2 (abnormal noise present—medium) was obtained in the third measurement. Therefore, it can be confirmed that when the frequency difference is smaller than −1.83 kHz, the probability of occurrence of the abnormal noise increases, and the magnitude of abnormal noise also increases.

From the above study results, it was found that as the frequency difference increases, transmission loss occurs in the ultrasonic vibration. As a result, it was confirmed that as the value of the effective electric power increases, part of the energy that becomes the transmission loss is externally released as an abnormal noise. Therefore, it was confirmed important to reduce the frequency difference in the use state of the handpiece 12 and in the initial state before using the handpiece 12 in order to realize efficient transmission of the ultrasonic vibration.

According to the present embodiment, the treatment device 11 includes a vibrator capable of ultrasonically vibrating, a front mass portion 32 having a first resonance frequency and connected to the vibrator in a manner capable of transmitting ultrasonic vibration, a treatment probe for treating a subject and having a second resonance frequency that is higher than the first resonance frequency of the front mass portion 32, and a connection portion that connects a distal end surface of the front mass portion and a proximal end surface of the treatment probe by a pressing force, and serves as an antinode position when vibrating at the first resonance frequency.

According to this configuration, while using the treatment device, the resonance frequency of the treatment probe decreases to a frequency equivalent to the resonance frequency of the front mass portion 32. As a result, even during use, the resonance frequencies of the front mass portion 32 and the treatment probe become equal to each other, which prevents transmission loss of the ultrasonic vibration from occurring. As a result, the ultrasonic vibration can be efficiently transmitted from the vibrator to the treatment probe.

In the present embodiment, the relationship of the first resonance frequency<the second resonance frequency<the first resonance frequency+1.5 kHz is established. According to this configuration, the resonance frequency of the treatment probe side would not greatly vary with respect to the resonance frequency of the front mass portion 32 side in either the initial state or the use state. Therefore, the ultrasonic vibration can be efficiently transmitted from the front mass portion 32 to the treatment probe without increasing the power for driving the vibrator, or the occurrence of abnormal noise at the connection portion.

The probe 16 and the vibration generation unit 26 are fixed by non-threaded connection. According to this configuration, the probe 16 and the vibration generation unit 26 can be fixed without using screws; therefore, torque management using a torque wrench or the like when performing screw fixing would become unnecessary. As a result, when fixing the probe 16 to the vibration generation unit 26, work burden can be reduced for an operator. In the present embodiment, for example, the probe 16 and the vibration generation unit 26 are fixed by an abutting structure using a cam (cam type fixing).

The probe 16 and the vibration generation unit 26 are connected in the vicinity of the antinode position 43 of the ultrasonic vibration. Generally, when ultrasonic vibrations are transmitted from one member to another member, transmission loss can be reduced by arranging the antinode position of the ultrasonic vibration on the boundary surface between the two members. According to the above configuration, the antinode position 43 of the ultrasonic vibration can be arranged in the vicinity of the boundary surface B between the probe 16 and the vibration generation unit 26, which would reduce the transmission loss of the ultrasonic vibration. As a result, the ultrasonic vibration can be efficiently transmitted from the vibration generation unit 26 to the probe 16.

The temperature of the probe 16 rises higher than the initial state in the use state, and the resonance frequency of the probe 16 decreases from the second resonance frequency. According to this configuration, in the case where the rise in temperature of the probe 16 causes the resonance frequency of the probe 16 to change, the transmission loss of the ultrasonic vibration can be reduced, and the ultrasonic vibration can be efficiently transmitted from the vibration generation unit 26 to the probe 16.

The treatment device comprises a high-frequency energy supply unit capable of supplying high-frequency energy to the treatment probe, and the ultrasonic vibration and the high-frequency energy can be simultaneously transmitted to the treatment probe. According to this configuration, it is possible to supply two types of energy including ultrasonic vibration energy and high-frequency energy to the treatment probe.

As a result, the treatment device 11 having further enhanced incision, resection, or coagulation performance can be provided in comparison to, for example, the treatment device 11 that supplies only one type of energy.

Second Embodiment

Figure 8:
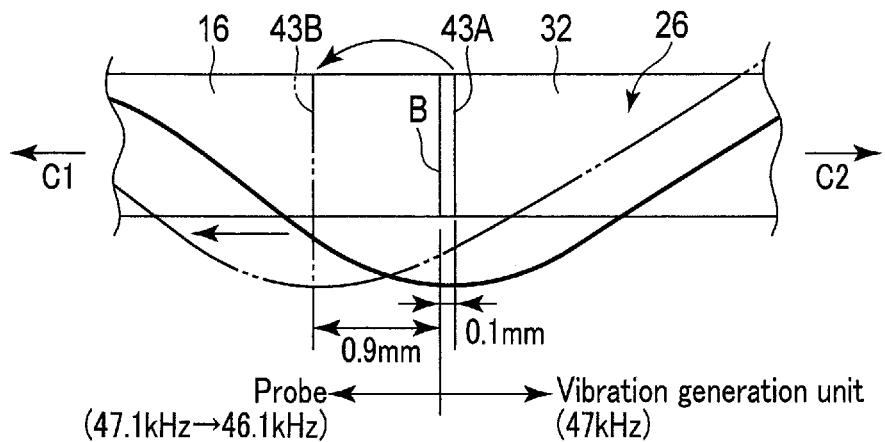
FIG. 8 is a schematic diagram showing an ultrasonic vibration wave (a waveform at the moment of a maximum amplitude) transmitted through a probe and a sheath member of a treatment device of a second embodiment.

With reference to FIG. 8, a treatment device of a second embodiment will be explained. A treatment device 11 of the second embodiment differs from the treatment device of the first embodiment in that a second resonance frequency of a probe 16 in the initial state and a position of an antinode position 43 of an ultrasonic vibration transmitted from a vibration generation unit 26 to the probe 16 are different. The other parts are the same as those of the first embodiment. Therefore, mainly the parts different from the first embodiment will be explained, and illustration or explanation of parts common to the first embodiment will be omitted. The treatment device 11 of the present embodiment is used at the same time as other forceps, scalpels and the like, and is a treatment device suitable for treatment with low frequency of use in one surgical operation, such as being used at pinpoint during surgery.

As shown in FIG. 8, the probe 16 (treatment probe) is formed in a rod shape by, for example, a biocompatible metal material (for example, titanium, a titanium alloy, duralumin, and stainless steel).

The second resonance frequency of the probe 16 is designed to be 47.1 kHz which is higher than a resonance frequency of a front mass portion 32 in an initial state (a state before a surgeon uses the treatment device 11).

A boundary surface B (joint surface) between the probe 16 and the front mass portion 32 is designed to be positioned at the vicinity of the antinode position 43 of the ultrasonic vibration propagating therethrough. More specifically, as shown in FIG. 8, an antinode position 43A of the ultrasonic vibration in an initial state is designed to be set at a position shifted 0.1 mm from the boundary surface B toward a proximal end direction C2 side (toward the vibration generation unit 26 side). At this time, the ultrasonic vibration transmitted through the vibration generation unit 26 and the probe 16 has a waveform as indicated by a solid line at the moment of the maximum amplitude.

Next, with reference to FIG. 8, an operation of the treatment device 11 of the present embodiment will be explained. In the present embodiment, the resonance frequency of the front mass portion 32 is 47 kHz (first resonance frequency). The resonance frequency of the probe 16 is 47.1 kHz (second resonance frequency) in the initial state. The antinode position 43A of the ultrasonic vibration in the initial state is at a position deviated 0.1 mm from the boundary surface B of the vibration generation unit 26 and the probe 16 toward the vibration generation unit 26 side. Although the antinode position 43A of the ultrasonic vibration is deviated from the boundary surface B in the initial state, the transmission loss of the vibration at the boundary surface B is minor because the displacement amount is minute.

When the surgeon starts treatment and the treatment instrument 11 is continuously used, the temperature of the probe 16 instantaneously rises up to, for example, 200 to 400° C. at the maximum. In the case where the temperature of the probe 16 becomes high in the above manner, the Young's modulus of the probe 16 changes, and the resonance frequency of the probe 16 drops from 47.1 kHz (second resonance frequency) to, for example, 46.1 kHz at a minimum value (an amount by which the resonance frequency decreases varies depending on the temperature rise amount of the probe 16). When the resonance frequency of the probe 16 decreases to, for example, 46.1 kHz, an entire third resonance frequency of the combination of the front mass portion 32 and the probe 16 also decreases, and the wave of the ultrasonic vibration transmitted through the vibration generation unit 26 and the probe 16 is shifted toward the probe 16 side to a position indicated by a two-dot chain line at the maximum. Therefore, an antinode 43B of the ultrasonic vibration also moves 0.9 mm at the maximum from the boundary surface B (joint surface) of the probe 16 and the vibration generation unit 26 to a position shifted toward the probe 16 side.

However, the shift amount from the antinode position 43A to the antinode position 43B is a maximum value. Therefore, in a case where the frequency of use is low during the surgical operation as in the treatment device 11 of the present embodiment, an average value of the temperature of the probe 16 in the surgical operation is often in the range of 20 to 100° C. Therefore, although the antinode position 43 of the ultrasonic vibration transmitted through the vibration generation unit 26 and the probe moves toward the probe 16 side, it is often arranged in the vicinity of the boundary surface B. Therefore, during the treatment, since the displacement amount of the antinode 43 of the ultrasonic vibration from the boundary surface B is minute, the transmission loss of the vibration at the boundary surface B is minor. Therefore, in the present embodiment, since the antinode positions 43A and 43B of the ultrasonic vibration can be arranged in the vicinity of the boundary surface B before and after the change in the resonance frequency on the probe 16 side, the vibration transmission loss at the boundary surface B can be reduced. In addition, in the present embodiment, the probe 16 and the vibration generation unit 26 are designed so as to satisfy the relationship of the first resonance frequency<the second resonance frequency<the first resonance frequency+1.5 kHz.

Third Embodiment

Figure 9:
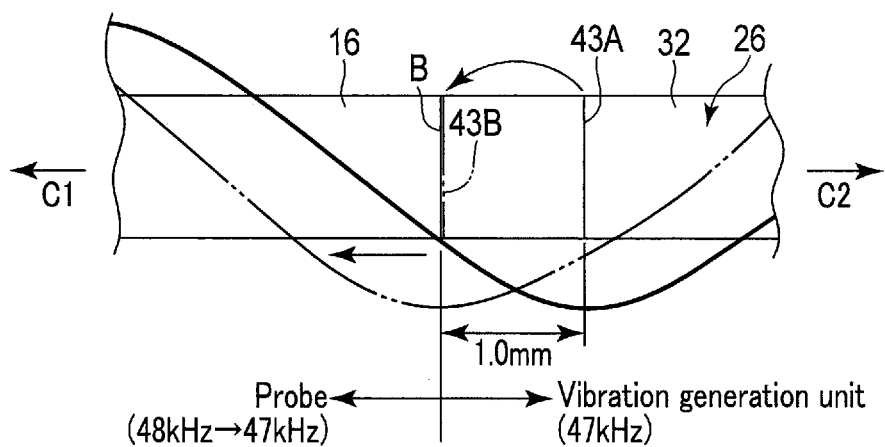
FIG. 9 is a schematic diagram showing an ultrasonic vibration wave (a waveform at the moment of a maximum amplitude) transmitted through a probe and a sheath member of a treatment device of a third embodiment.

With reference to FIG. 9, a treatment device of a third embodiment will be explained. A treatment device 11 of the third embodiment differs from the first embodiment in that a second resonance frequency of a probe 16 in an initial state and a position of an antinode position 43 of an ultrasonic vibration transmitted from a vibration generation unit 26 to the probe 16 are different. The other parts are the same as those of the first embodiment.

Therefore, mainly the parts different from the first embodiment will be explained, and illustration or explanation of parts common to the first embodiment will be omitted. The treatment device 11 of the present embodiment is a treatment device suitable to be used continuously over long hours under a severe condition, such as a treatment of a mammary gland, that is, for a procedure frequently used in one surgical operation.

As shown in FIG. 9, the probe 16 (treatment portion) is formed in a rod shape by, for example, a biocompatible metal material (for example, titanium, titanium alloy, duralumin, and stainless steel). The second resonance frequency of the probe 16 is designed to be 48 kHz, which is higher than a first resonance frequency of a front mass portion 32 in the initial state (a state before a surgeon uses the treatment device 11).

A boundary surface B (joint surface) of the probe 16 and the front mass portion 32 is designed to be positioned in the vicinity of the antinode position 43 of the ultrasonic vibration propagating therethrough. More specifically, as shown in FIG. 9, an antinode position 43A of the ultrasonic vibration in the initial state is designed to be set at a position moved 1.0 mm from the boundary surface B toward a proximal end direction C2 side (toward the vibration generation unit 26 side).

Next, with reference to FIG. 9, an operation of the treatment device 11 of the present embodiment will be explained. In the present embodiment, the resonance frequency of the vibration generation unit 26 (front mass portion 32) is 47 kHz (first resonance frequency). Furthermore, the resonance frequency of the probe 16 is 48 kHz (second resonance frequency) in the initial state.

In the initial state, an antinode position 43A of the ultrasonic vibration (indicated by a solid line) transmitted through the vibration generation unit 26 and the probe 16 is deviated 1.0 mm from the boundary surface B of the vibration generation unit 26 and the probe 16 toward the vibration generation unit 26 side. In the initial state, although the antinode position 43A of the ultrasonic vibration is deviated from the boundary surface B, since the treatment device is used in a short time in a state where the temperature of the probe 16 does not rise, the transmission loss of the vibration at the boundary surface B is minor.

When the surgeon starts the treatment and the treatment device 11 is continuously used, the temperature of the probe 16 rises up to, for example, 200 to 400° C. at the maximum. In the case where the probe 16 reaches a high temperature in the manner described above, the Young's modulus of the probe 16 changes, and the resonance frequency of the probe 16 drops from 48 kHz (second resonance frequency) to, for example, 47 kHz at a minimum value (an amount by which the resonance frequency decreases varies depending on the temperature rise amount of the probe 16). When the resonance frequency of the probe 16 decreases to, for example, 47 kHz, an entire third resonance frequency of a combination of the front mass portion 32 and the probe 16 also decreases, and a wave of the ultrasonic vibration transmitted through the vibration generation unit 26 and the probe 16 shifts toward the probe 16 side to a position indicated by a two-dot chain line at the maximum. Therefore, an antinode position 43B of the ultrasonic vibration also moves to the boundary surface B (joint surface) of the probe 16 and the vibration generation unit 26 at the maximum. Under severe conditions where the treatment device is continuously used over long hours as in the present embodiment, the device is continuously used in a state where the temperature of the probe 16 remains high. Therefore, the antinode position 43B of the ultrasonic vibration substantially coincides with the boundary surface B during the treatment, and the transmission loss of the vibration at the boundary surface B becomes minor. Therefore, in the present embodiment, under severe conditions of, such as, continuous usage, the antinode position 43 of the ultrasonic vibration can coincide with the boundary surface B, which would reduce the transmission loss of the vibration at the boundary surface B. In addition, in the present embodiment, the probe 16 and the vibration generation unit 26 are designed to satisfy the relationship of the first resonance frequency<the second resonance frequency<the first resonance frequency+1.5 kHz.

According to the present embodiment, in the initial state, the antinode 43A of the ultrasonic vibration is at a position moved by a distance of 1 mm or less from the connection portion to the front mass portion 32 side. According to this configuration, the antinode position 43 can be positioned in the vicinity of the boundary surface B in both the initial state and the use state, which prevents the transmission loss of the ultrasonic vibration from occurring, and allows the ultrasonic vibration to be efficiently transmitted from the front mass portion 32 to the treatment probe.

Modified Examples of First Embodiment

With reference to FIG. 10 to FIG. 18, each modified example (first to eighth modified examples) of the treatment device 11 of the first embodiment will be explained below. Here, mainly the parts different from the first embodiment will be explained, and illustrations or explanations of parts common to the first embodiment will be omitted.

First Modified Example

As shown in FIG. 10, a probe unit 21 includes an annular member 61. The annular member 61 is provided at a position between a flange portion 67 of a probe 16 and a case 35. The annular member 61 is made of a material having a low friction property or a lubricating property. More specifically, for example, it is made of a fluorine-based resin (PTFE, PFA). The annular member 61 is provided at a node position 62 of an ultrasonic vibration transmitted to the probe 16. At the node position 62, the amplitude of the ultrasonic vibration is minimized. However, also at this node position 62, a minute vibration is usually generated, causing friction to occur between the probe 16 and the case 35.

According to this modified example, since the low friction annular member 61 is interposed between the probe 16 and the case 35, the friction generated between the probe 16 and the case 35 at the node position 62 can be reduced.

Second Modified Example

As shown in FIG. 10, a probe unit 21 includes an annular member 61. The annular member 61 is provided at a position between a flange portion 67 of a probe 16 and a case 35. Unlike the first modified example, in the present modified example, the annular member 61 is made of a rubbery elastic material. More specifically, it is made of, for example, a rubber material (silicone rubber, fluoro-rubber). The annular member 61 is provided at a node position 62 of an ultrasonic vibration transmitted to the probe 16. At the node position 62, the amplitude of the ultrasonic vibration is minimized. However, even at this node position 62, minute vibration is usually generated.

According to the present modified example, since the elastic annular member 61 is interposed between the probe and the case 35, the vibration of the probe 16 is absorbed at the node position 62, allowing the vibration transmitted from the probe 16 to the case 35 side to be reduced. If the annular member 61 is made of a low friction rubber such as a fluoro-rubber, the annular member 61 can have both the low friction property as referred to in the first modified example and the rubber-like elasticity of the present modified example.

Third Modified Example

Figure 11:
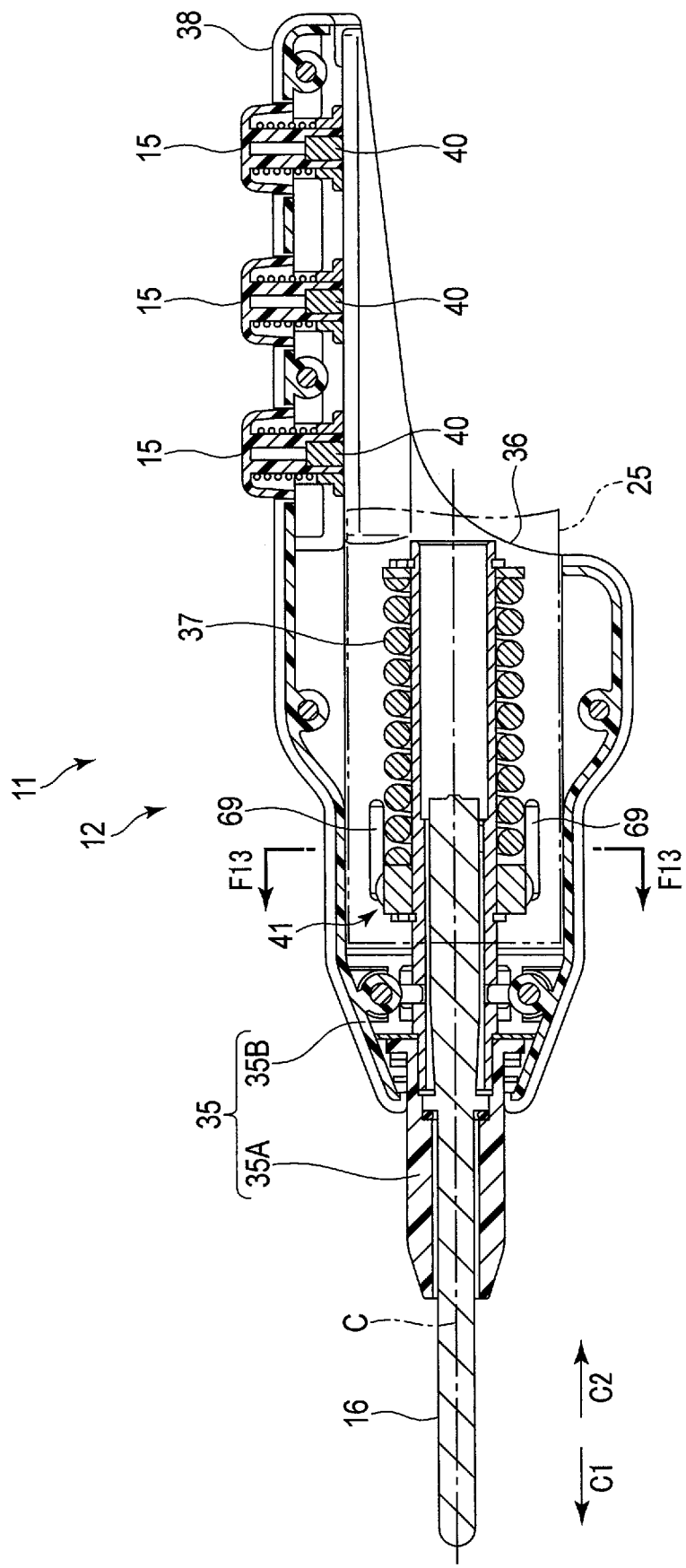
FIG. 11 is a cross-sectional view showing a treatment device of a third modified example taken along a plane along a central axis.

As shown in FIG. 11 and FIG. 12, a probe unit 21 has a pair of annular low friction members 60. The pair of low friction members 60 have the same shape (a flat washer shape, a ring shape having a rectangular cross section). The pair of low friction members 60 are provided between a first portion 35A configuring a rotation knob of a case 35 and a second portion 35B configuring a main body portion of the case 35. More specifically, as shown in FIG. 12, the low friction member 60 is provided between a flange-like portion 58 on a proximal end direction C2 side of the first portion 35A, and a receiving portion 59 protruding inward of the second portion 35B. The low friction member 60 is made of a fluorine-based resin (PTFE, PFA). The pair of low friction members 60 is arranged overlapping each other in a longitudinal direction C. When a probe 16 is pressed against a front mass portion 32 with a predetermined pressure and connected thereto, a counteraction thereof also causes the probe 16 to be pressed against the low friction member 60. In the present modified example, by using the two low friction members 60 in an overlapped manner, a rotational force (a frictional force occurring between the first portion 35A and the second portion 35B) necessary for rotating the probe 16 by holding the first portion 35A as a rotation knob can be reduced. This allows a doctor to smoothly rotate the probe 16 with a relatively small force.

Furthermore, in the present modified example, a plurality of protrusions 69 are provided on an inner peripheral surface of the cylindrical main body portion of the second portion 35B. The protrusion 69 extends in the longitudinal direction C by a predetermined length. As shown in FIG. 13, the protrusion 69 has an arcuate cross-sectional shape when cut by a surface intersecting the longitudinal direction C. The top portion of the protrusion 69 can make a point contact with respect to an outer peripheral surface of a housing 25 (a line contact with respect to the longitudinal direction C) on a grip unit 22 side. Therefore, the contact area between the housing 25 and the second portion 35B can be reduced. This allows the frictional force acting between the outer peripheral surface of the housing 25 and the inner peripheral surface of the second portion 35B to be reduced when the grip unit 22 is inserted into and retracted from the probe unit 21. It is also preferable to form one of the housing 25 and the protrusion 69 of a fluorine-based resin (PTFE, PFA) to further reduce the frictional force.

Fourth Modified Example

Figure 14:
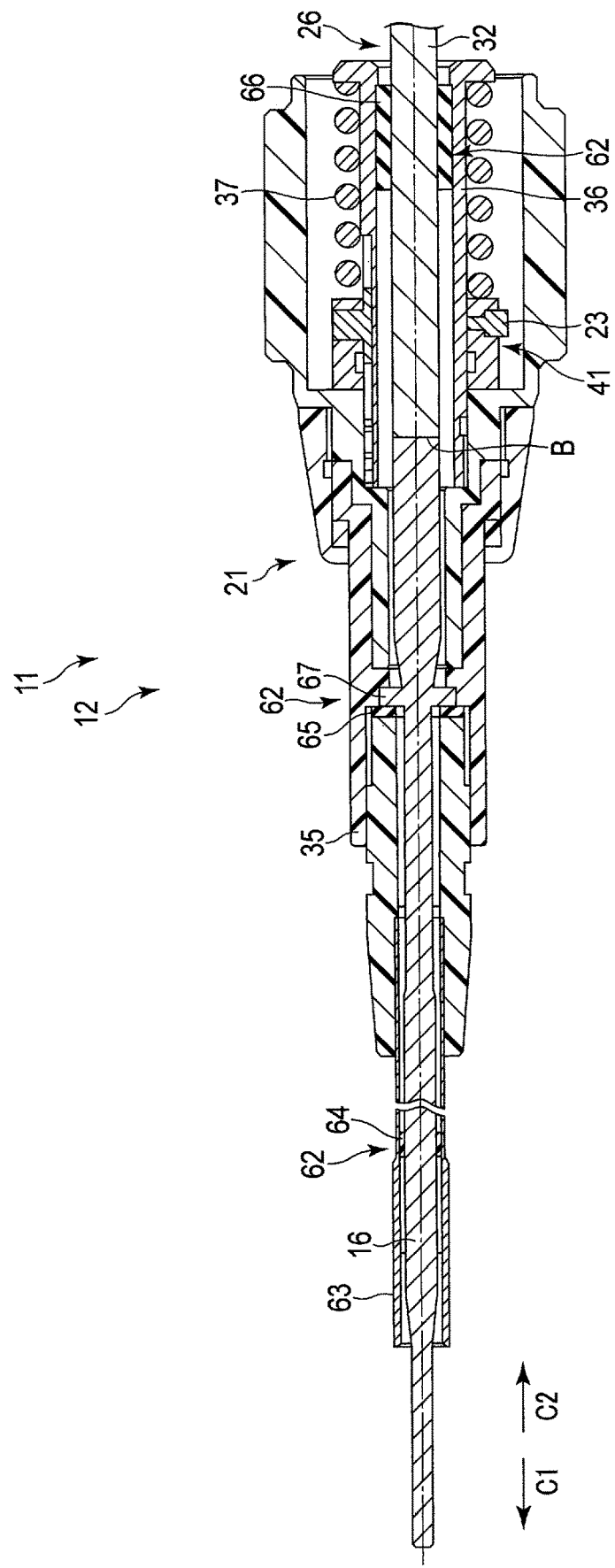
FIG. 14 is a cross-sectional view of a treatment device of a fourth modified example taken along a plane along a central axis.

As shown in FIG. 14, a probe unit 21 includes a cylindrical sheath 63 for protecting a probe 16, a first annular member 64 provided between the probe 16 and the sheath 63, a second annular member 65 interposed between the probe 16 and a case 35, and a third annular member 66 interposed between a front mass portion 32 and the case 35. Each of the first to third annular members 64-66 is made of a material having a low friction property or a lubricating property. More specifically, for example, they are made of a fluorine-based resin (PTFE, PFA). The first annular member 64 has a cylindrical shape and supports the probe 16 at a center position of the sheath 63. The first annular member 64 is provided at a node position 62 of the ultrasonic vibration transmitted to the probe 16. The first annular member 64 is capable of sealing (seal) the inside of the sheath 63 on a proximal end direction C2 side, so as to prevent fragments of living tissue produced by the treatment, or liquid and the like from entering the inside of the sheath 63 (or the inside of the case 35).

The second annular member 65 has a disc shape with a through hole at a center portion, and abuts a flange portion 67 of the probe 16. In the same manner as the first annular member 64, the second annular member 65 is provided at the node position 62 of the ultrasonic vibration transmitted through the probe 16. The third annular member 66 has a cylindrical shape and holds the front mass portion 32 at a center position of a cylindrical member 36 so that the center of the front mass portion 32 does not deviate from the center of the probe 16. The third annular member 66 is provided at the node position 62 of the ultrasonic vibration transmitted through the front mass portion 32.

At the node position 62 of the ultrasonic vibration, the amplitude of the ultrasonic vibration transmitted through the probe 16 or the front mass portion 32 is minimized. However, even at this node position 62, minute vibrations are usually generated, causing friction to occur between the probe 16 and the case 35, between the probe 16 and the sheath 63, or between the front mass portion 32 and the cylindrical member 36.

According to the present modified example, the first to third annular members 64 to 66 having low friction properties are interposed between the probe 16 and the case 35. Therefore, at the node position 62, friction generated between the probe 16 and the case 35, between the probe 16 and the sheath 63, or between the front mass portion 32 and the cylindrical member 36 can be reduced. If the first to third annular members 64 to 66 are made of a low friction rubber such as a fluoro-rubber, the first to third annular members 64-66 can have both the low friction property as referred to in the first modified example and the rubber-like elasticity of the second modified example.

Fifth Modified Example

Figure 15:
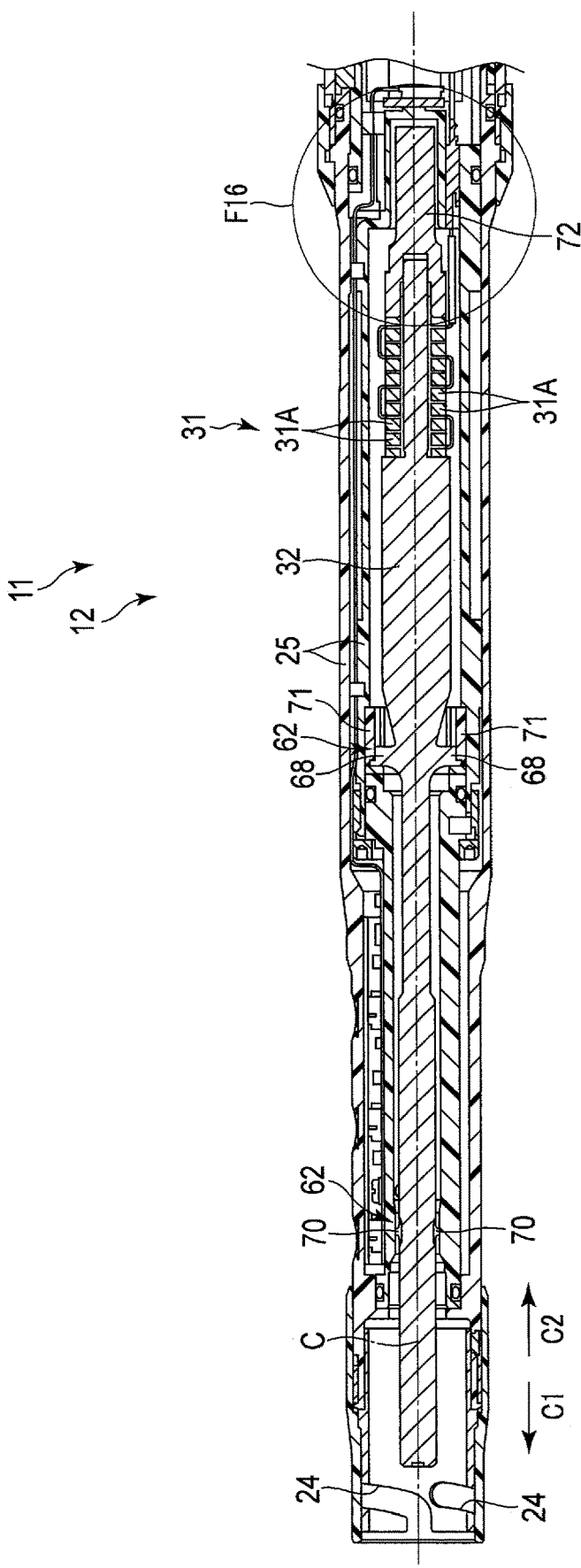
FIG. 15 is a cross-sectional view of a treatment device of a fifth modified example taken along a plane along a central axis.

As shown in FIG. 15, a grip unit 22 includes a substantially cylindrical housing 25 configuring an outer shell, and a vibration generation unit 26 accommodated in the housing 25. The vibration generation unit 26 includes an ultrasonic transducer 31 accommodated in the housing 25, and a front mass portion 32 connected to the ultrasonic transducer 31. The front mass portion 32 has a flange-like portion 68. The grip unit 22 has a cylindrical support member 71 between the flange-like portion 68 and the housing 25.

Each of the support members 71 is made of a material having a low friction property or a lubricating property. More specifically, it is made of, for example, a fluorine-based resin (PTFE, PFA). The support member 71 has a cylindrical shape and supports the front mass portion 32 at a center position of the housing 25. The support member 71 is provided at a node position 62 of an ultrasonic vibration transmitted through the front mass portion 32. An annular seal member 70 is provided at a node position 62 on a distal end direction C1 side of the ultrasonic vibration transmitted through the front mass portion 32. The seal member 70 supports the distal end side of the front mass portion 32 at the center position of the housing 25 and prevents liquid or pieces of treated biological tissue from entering into the housing 25. The seal member 70 is made of, for example, a fluorine-based resin (PTFE, PFA).

At the node position 62 of the ultrasonic vibration, the amplitude of the ultrasonic vibration transmitted through the front mass portion 32 is minimized. However, even at this node position 62, minute vibrations are usually generated, causing friction to occur between the front mass portion 32 and the housing 25.

According to the present modified example, since the low frictional support member 71 is interposed between the front mass portion 32 and the housing 25, the friction generated between the front mass portion 32 and the housing 25 can be reduced at the node position 62. If the support member 71 is made of a low friction rubber such as a fluoro-rubber, the support member 71 can have both the low friction property as referred to in the first modified example and the rubber-like elasticity of the second modified example.

Sixth Modified Example

Figure 16:
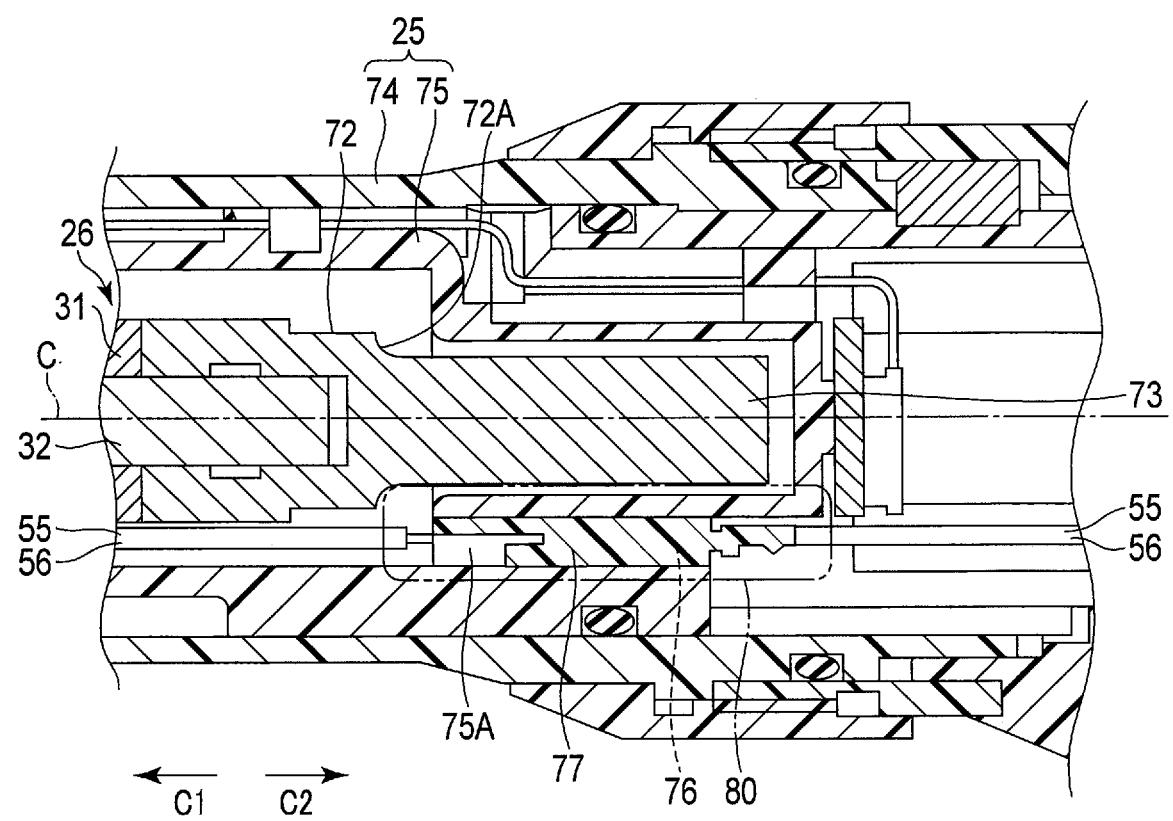
FIG. 16 is an enlarged view of a portion F16 shown in FIG. 15, and is a cross-sectional view showing a treatment device of a sixth modified example.

FIG. 16 is an enlarged view of F16 shown in FIG. 15 of a fourth modified example. As shown in FIG. 16, a grip unit 22 includes a substantially cylindrical housing 25 configuring an outer shell, and a vibration generation unit 26 accommodated in the housing 25. The vibration generation unit 26 includes an ultrasonic transducer 31 accommodated in the housing 25, a front mass portion 32 connected to the ultrasonic transducer 31, and a fixing member 72 (back mass) for fixing the ultrasonic transducer 31 to the front mass portion 32. The fixing member 72 has a female screw portion, and is screw-fixed to a male screw portion provided on a proximal end surface 32A of the front mass portion 32.

The fixing member 72 has a stepped part 72A in the middle thereof, and a diameter of a portion of a head part 73 is formed to be small. The housing 25 has an outer housing 74 configuring the outer shell and an inner housing 75 surrounding the vibration generation unit 26. The interior of the inner housing 75 has a so-called vapor-tight structure so that high temperature and high pressure steam does not enter inside the inner housing 75 even when the grip unit 22 is autoclaved. The inner housing 75 is provided with a through-hole portion 75A. Inside the through-hole portion 75A, an electrical connection portion 76 and an insulating resin portion 77 surrounding the electrical connection portion 76 are contained. Two first conducting wires 55 and one second conducting wire 56 are passed through the electrical connection portion 76, and an electric contact point 80 of each of the conducting wires is formed on the electrical connection portion 76. The resin portion 77 hermetically seals the through-hole portion 75A with a so-called vapor-tight structure, and prevents steam from entering into the inner housing 75 from the through-hole portion 75A during the autoclave process.

According to the present modified example, the diameter of the head part 73 of the fixing member 72 is made small, which allows the electrical connection portion 76 to be arranged in a space made free by such diameter. Therefore, the grip unit 22 can be prevented from increasing in size, which allows the treatment device 11 to be made compact.

Seventh Modified Example

Figure 17:
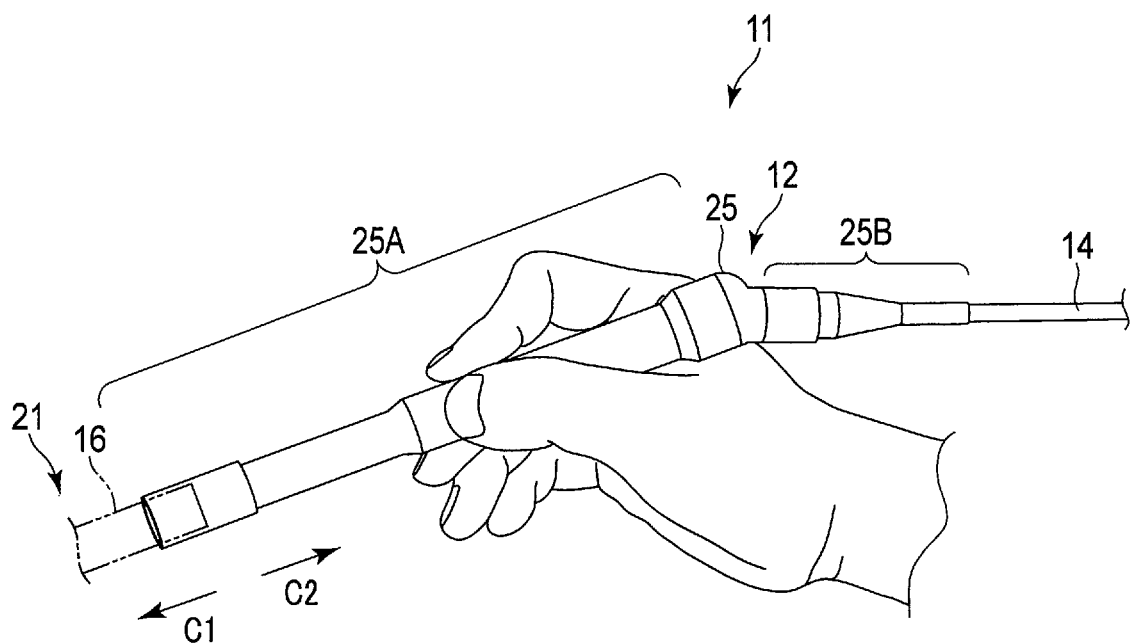
FIG. 17 is a perspective view showing a treatment device of a seventh modified example.

As shown in FIG. 17, a grip unit 22 includes a substantially cylindrical housing 25 that configures an outer shell. The housing 25 has a main body portion 25A and a bent portion 25B bent with respect to the main body portion 25A. The bent portion 25B is provided at a position connected to a cable 14. Therefore, the housing 25 is formed in a shape alongside the hand of an operator by the main body portion 25A and the bent portion 25B.

In the present modified example, since the bent portion 25B is provided in the housing 25, a tension acting through the cable 14 can be directed in a direction along the so-called back of the hand. Therefore, the influence of the tension acting on a handpiece 12 through the cable 14 can be further reduced in comparison to the case in which the housing 25 is linearly formed. Thereby, workability of the operator can be improved.

Eighth Modified Example

Figure 18:
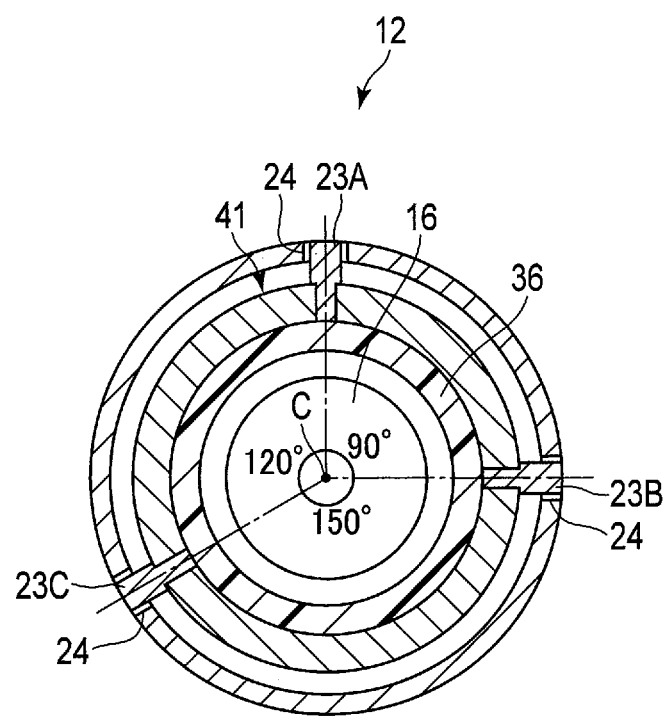
FIG. 18 is a cross-sectional view taken along a line F18-F18 shown in FIG. 10, and is a cross-sectional view showing a treatment device of an eighth modified example.

FIG. 18 is a cross-sectional view taken along the line F18-F18 shown in FIG. 10 of the first modified example. The probe unit 21 includes a probe 16, a case 35 covering the periphery of the probe 16, a cylindrical member 36 integrally provided with the probe 16 and the case 35, a spring member 37 provided around the cylindrical member 36, and a pin unit 41 slidably movable with respect to the cylindrical member 36 and pressed toward a distal end direction C1 by the spring member 37. The pin unit 41 has first to third pins 23A to 23C protruding in a radial direction of the probe 16. The first to third pins 23A to 23C are arranged asymmetrically with respect to a central axis C. An angle formed by the first pin 23A and the second pin 23B is, for example, 90°, an angle formed by the second pin 23B and the third pin 23C is, for example, 150°, and an angle formed by the third pin 23C and the first pin 23A is, for example, 120°. Note that these angles are merely examples, and it goes without saying that other angles are also acceptable as long as each pin is arranged asymmetrically with respect to the central axis C.

According to the present modified example, since the first to third pins 23A to 23C are arranged in a so-called asymmetrical manner with respect to the central axis C, it is possible to fix the probe unit 21 at a correct angle with respect to a grip unit 22. Thereby, an operation button 15 on the probe unit 21 side can be aligned with a detection unit 27 on the grip unit 22 side. As a result, a problem of the detection unit 27 failing to detect an operation of the operation button 15 can be prevented.

The present invention is not limited to the above-described embodiments, and can be appropriately modified in practice, without departing from the gist of the invention. In addition, it is, of course, possible to combine treatment devices of each of the above-mentioned embodiments and modified examples to configure one treatment device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
a vibrator capable of ultrasonically vibrating;
a front mass portion having a first resonance frequency and connected to the vibrator in a manner capable of transmitting ultrasonic vibration;
a treatment portion probe for treating a subject and having a second resonance frequency that is higher than the first resonance frequency of the front mass portion; and
a connection portion connecting a distal end surface of the front mass portion and a proximal end surface of the treatment portion probe in a non-threaded manner by a pressing force, and serving as an antinode position when vibrating at the first resonance frequency, wherein
the treatment device is configured to satisfy a relationship of the first resonance frequency<the second resonance frequency<the first resonance frequency+1.5 kHz.

2. The treatment device according to claim 1, wherein, in an initial state, the antinode position of the ultrasonic vibration is at a position moved by a distance of 1 mm or less from the connection portion toward a front mass portion side.

3. The treatment device according to claim 1, comprising a high-frequency energy supply unit capable of supplying high-frequency energy to the treatment portion probe, wherein
the ultrasonic vibration and the high-frequency energy can be simultaneously transmitted to the treatment portion probe.

4. The treatment device according to claim 1, wherein the treatment portion probe and the front mass portion are connected along a longitudinal axis, and at least a proximal end surface of the treatment portion probe or a distal end surface of the front mass portion is a plane surface that is orthogonal to the longitudinal axis.

5. The treatment device according to claim 1, comprising:
a probe unit in which the treatment portion probe is provided;
a grip unit in which the vibrator is provided;
a pin provided in the probe unit; and
a receiving portion for receiving the pin, provided in the grip unit.

6. The treatment device according to claim 1, wherein the treatment portion probe and the front mass portion are abutted and fixed by using a cam.

7. A treatment portion probe for treating a subject, which, in a manner capable of transmitting ultrasonic vibration, is connected to a vibrator capable of ultrasonically vibrating, and has a second resonance frequency that is higher than a first resonance frequency of a front mass portion having the first resonance frequency, wherein
a proximal end surface of the treatment portion probe is connected to a distal end surface of the front mass portion in a non-threaded manner by a pressing force, and serves as an antinode position when vibrating at the first resonance frequency; and
the treatment portion probe is configured to satisfy a relationship of the first resonance frequency<the second resonance frequency<the first resonance frequency+1.5 kHz.

* * * * *